United States Patent
Lumgair et al.

(10) Patent No.: US 8,338,656 B2
(45) Date of Patent: Dec. 25, 2012

(54) SEPARATING OLEFIN STREAMS

(75) Inventors: David Ritchie Lumgair, Craddockville, VA (US); Michael Peter Nicoletti, Houston, TX (US); Ram Mallik, Houston, TX (US); Wadie Malaty, Houston, TX (US); Malcolm Pettigrew, Houston, TX (US)

(73) Assignees: Lummus Technology Inc., Bloomfield, NJ (US); ExxonMobil Chemical Patents Inc., Houston, TX (US)

( * ) Notice: Subject to any disclaimer, the term of this patent is extended or adjusted under 35 U.S.C. 154(b) by 210 days.

(21) Appl. No.: 12/681,336

(22) PCT Filed: Oct. 1, 2007

(86) PCT No.: PCT/US2007/021123
§ 371 (c)(1),
(2), (4) Date: Jul. 13, 2010

(87) PCT Pub. No.: WO2009/045186
PCT Pub. Date: Apr. 9, 2009

(65) Prior Publication Data
US 2010/0292521 A1    Nov. 18, 2010

(51) Int. Cl.
*C07C 7/00* (2006.01)
*C07C 1/02* (2006.01)

(52) U.S. Cl. ........ 585/809; 585/640; 585/642; 585/802; 585/639

(58) Field of Classification Search .......................... None
See application file for complete search history.

(56) References Cited

U.S. PATENT DOCUMENTS

| | | |
|---|---|---|
| 3,258,455 A | 6/1966 | Natta et al. |
| 3,305,538 A | 2/1967 | Natta |
| 3,364,190 A | 1/1968 | Emrick |
| 3,645,992 A | 2/1972 | Elston |
| 4,076,698 A | 2/1978 | Anderson et al. |
| 4,243,691 A | 1/1981 | Mohlenkamp, Jr et al. |
| 4,302,565 A | 11/1981 | Goeke et al. |
| 4,310,440 A | 1/1982 | Wilson et al. |
| 4,567,029 A | 1/1986 | Wilson et al. |
| 4,659,685 A | 4/1987 | Coleman, III et al. |
| 5,421,167 A | 6/1995 | Verma |
| 5,892,079 A | 4/1999 | Wilson, Jr. |
| 6,395,952 B1 | 5/2002 | Barchas |
| 6,441,261 B1 | 8/2002 | Kuechler et al. |

(Continued)

FOREIGN PATENT DOCUMENTS
CA    2497943 A1    1/2006
(Continued)

OTHER PUBLICATIONS
International Search Report issued in PCT/US07/21123, mailed on Mar. 6, 2008, 2 pages.
(Continued)

*Primary Examiner* — Tam M Nguyen
(74) *Attorney, Agent, or Firm* — Osha • Liang LLP

(57) ABSTRACT

This invention pertains to separating an olefin stream into at least two olefin streams. The olefin stream that is to be separated is low in diene composition, which allows the olefin stream to be compressed at a relatively high temperature without causing fouling problems in the compressor system. The invention is particularly relevant to separating olefins obtained from an oxygen to olefins unit.

22 Claims, 1 Drawing Sheet

U.S. PATENT DOCUMENTS

| | | |
|---|---|---|
| 6,444,869 B2 | 9/2002 | Senetar et al. |
| 6,637,237 B1 | 10/2003 | Wei et al. |
| 7,855,312 B2 | 12/2010 | Borgmann et al. |
| 2005/0033104 A1 | 2/2005 | Van Egmond et al. |
| 2006/0004242 A1* | 1/2006 | Verma et al. .................. 585/809 |

FOREIGN PATENT DOCUMENTS

| | | |
|---|---|---|
| JP | 8302360 A | 11/1996 |
| JP | 11140461 A | 5/1999 |
| JP | 2005505612 A | 2/2005 |

OTHER PUBLICATIONS

Written Opinion issued in PCT/US07/21123, mailed on Mar. 6, 2008, 5 pages.

Office Action issued Dec. 13, 2011 in corresponding Canadian application No. 2,701,268 (3 pages).

Office action issued Nov. 3, 2011 by the Korean Intellectual Property Office in corresponding Korean application No. 10-2010-7009606 (13 pages).

Written Opinion issued in corresponding Singapore application No. 201002230-9, mailed on Apr. 20, 2011 (4 pages).

Notification of Reasons for Rejection issued Sep. 25, 2012 in corresponding Japanese application No. 2010-527918 (7 pages).

First Office Action dated Aug. 28, 2012 in corresponding Chinese Patent Application No. 200780101343.5 (with correspondence reporting same) (8 pages).

Second Office Action issued May 22, 2012 in corresponding Canadian application 2,701,268 (2 pages).

* cited by examiner

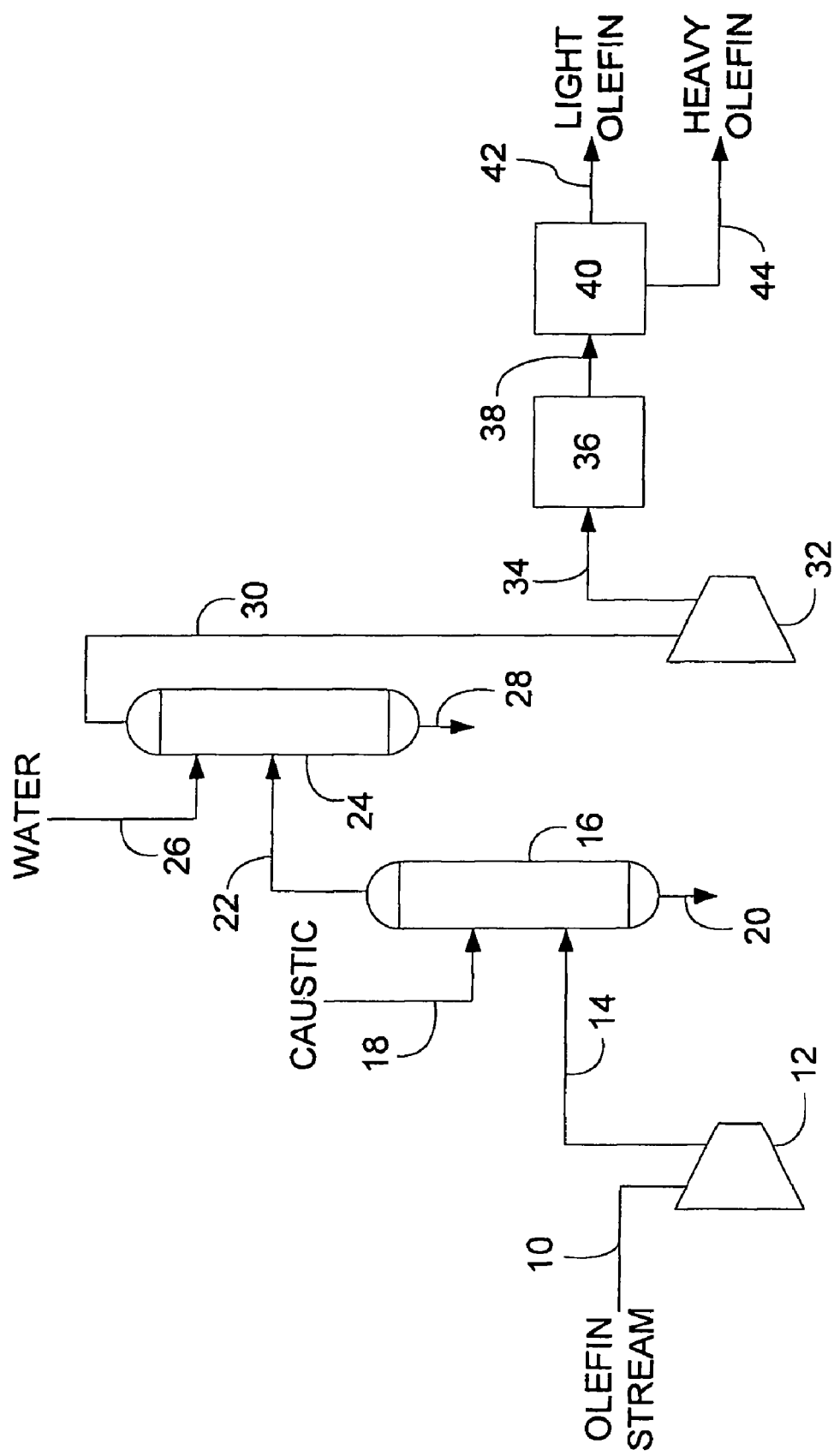

SEPARATING OLEFIN STREAMS

FIELD OF THE INVENTION

This invention relates to a process and system for separating an olefin stream into at least two olefin streams. More specifically, this invention relates to compressing an olefin product stream from an oxygenate to olefins unit and separating the compressed olefin stream into at least two olefin streams.

BACKGROUND OF THE INVENTION

Olefins are conventionally produced through the process of steam or catalytic cracking of various hydrocarbons. Olefins can also be produced by catalytically converting oxygenates to olefin compounds. The olefin product of such processes includes numerous olefin components (i.e., compounds), as well as certain non-olefin components, which have to be separated for further conversion to other chemical compounds such as olefin dimers, oligomers or polymers.

Conventional processes for separating olefin streams into other olefin component streams include compressing the olefin stream prior to separation into the other component streams. These processes typically involve multi-stage compression processes, which require several large compressors, and the compressed olefin stream is cooled after each stage with intercoolers.

U.S. Pat. No. 6,444,869 discloses one type of process for the separation and recovery of ethylene and heavier components from an oxygenate conversion process. The oxygenate conversion effluent stream, which comprises hydrogen, carbon dioxide, water, $C_2$ to $C_4$ hydrocarbons and oxygenates, is withdrawn from the oxygenate conversion reactor and passed to a multi-stage effluent compressor to raise the pressure of the oxygenate conversion effluent stream to provide a compressed effluent stream. The compressed effluent stream is passed to an oxygenate removal zone for the recovery of various oxygenates to provide an oxygenate depleted effluent stream. The oxygenate depleted effluent stream is passed to a carbon dioxide removal zone, and then to a dryer zone. The dry effluent is passed to a series of fractionation zones to separate the individual olefins into high purity products.

U.S. Pat. No. 6,441,261 discloses making an olefin stream by contacting oxygenate with a molecular sieve catalyst, compressing the olefin stream, and separating olefin components from the olefin stream. The olefin product stream is compressed in a compressor comprising one to four stages with cooling of the material between stages (intercooling). Higher compression ratios are considered to be desirable in that they result in less expensive compression modules, but are generally limited to the extent that contaminants present in the olefin stream can cause fouling at high temperatures. However, oxygenate conversion processes are considered to provide far fewer fouling contaminants, meaning that higher compression ratios can be achieved.

Improved processes for separating olefin streams into other olefin streams containing various olefin components are desired. In particular, processes which minimize compressor fouling or reducing the number of compressor stages used in separating olefin components in an olefin stream are sought.

SUMMARY OF THE INVENTION

This invention provides an improved process for separating an olefin stream into at least two olefin streams. The invention provides a way to minimize compressor fouling, as well as a way to reduce the number of compression stages.

In one embodiment, the invention comprises a process for separating an olefin stream into at least two olefin streams. The process comprises providing an olefin stream, wherein the olefin stream contains not greater than about 3.0 wt % dienes, based on total weight of the olefin stream. The olefin stream is compressed in a compressor system having a first stage and a second stage to obtain a compressed olefin stream, and the compressed olefin stream is separated into at least two olefin streams.

In another embodiment of the invention, the compressed olefin stream exits the first stage and the second stage at a temperature of not greater than 260° F. (127° C.). Preferably, the compressed olefin stream exits the first stage and the second stage at a temperature of not greater than 250° F. (121° C.). More preferably, the compressed olefin stream exits the first stage and the second stage at a temperature of from 220° F. (104° C.) to 260° F. (127° C.). Still more preferably, the compressed olefin stream exits the first stage and the second stage at a temperature of from 230° F. (110° C.) to 250° F. (121° C.).

In yet another embodiment of the invention, the compressed olefin stream exits the second stage at a pressure of at least 175 psia (1,207 kPa). Preferably, the compressed olefin stream exits the second stage at a pressure of at least 200 psia (1,379 kPa).

In another embodiment, the compressed olefin stream exits the first stage at a pressure of from 75 psia (517 kPa) to 150 psia (1,034 kPa). Preferably, the compressed olefin stream exits the first stage at a pressure of from 80 psia (552 kPa) to 140 psia (965 kPa).

The provided olefin can come from any source as long as the diene concentration is not too high. Such an olefin stream includes, as one example, an olefin stream made by contacting an oxygenate with a molecular sieve catalyst.

In one embodiment, the provided olefin stream comprises at least 50 wt % ethylene and propylene, based on total weight of the olefin stream. In another example, the provided olefin stream comprises from 50 wt % to 90 wt % ethylene and propylene, based on total weight of the olefin stream.

In another embodiment of the invention, the at least two olefin streams which are separated from the provided olefin include a light olefin stream and a heavy olefin stream. Desirably, the light olefin stream comprises at least one olefin selected from the group consisting of ethylene, propylene and butylenes, and the heavy olefin stream comprises olefins that have boiling points that are, on average, higher than those in the light olefin stream.

This invention includes an optional step of treating the compressed olefin stream between the first stage and the second stage of the compression system to remove acid gases prior to separating the compressed olefin stream into at least two olefin streams. Also optionally included is a step of washing the compressed olefin with water prior to separating into the at least two olefin streams. A step of drying the compressed olefin stream is also optionally included.

BRIEF DESCRIPTION OF THE DRAWING

FIG. 1 is a schematic drawing showing one embodiment of a flow scheme of the invention in which an olefin stream is compressed in a two stage compressor, and the compressed olefin stream is separated into a light olefin steam and a heavy olefin stream.

DETAILED DESCRIPTION OF THE INVENTION

I. Introduction

This invention provides a process for separating an olefin stream into at least two olefin streams. The process is performed with a minimal number of compression stages to compress the olefin stream to a pressure at which the compressed olefin stream can be efficiently separated into at least a light olefin stream and a heavy olefin stream.

The number of compression stages can be reduced in this invention, compared to that of conventional systems, since the amount of diene components in the olefin stream that is to be compressed is limited. By limiting the amount of dienes in the olefin stream, the compression system can be operated at higher than conventional temperatures, with a significant reduction in compressor fouling problems. An olefin stream having a high diene concentration will cause significant compressor fouling problems at high compression temperatures.

II. Olefin Stream that is to be Compressed

In this invention, an olefin stream is compressed and separated into at least two olefin streams. The two olefin streams preferably include at least a light olefin stream and a heavy olefin stream. The light olefin stream comprises at least one olefin selected from the group consisting of ethylene, propylene and butylene. The heavy olefin stream comprises olefins that have boiling points that are, on average, higher than those in the light olefin stream.

The olefin stream that is to be compressed and separated contains not greater than about 3.0 wt % dienes, particularly dienes such as butadienes and pentadienes, based on total weight of the olefin stream. Preferably, the olefin stream that is to be separated contains not greater than about 2.0 wt % dienes, more preferably not greater than about 1.0 wt % dienes, and most preferably not greater than about 0.5 wt % dienes, based on total weight of the olefin stream.

The olefin stream that is to be compressed and separated into olefin components is optionally relatively low in water content, as too much water can cause problems in compressor efficiency and/or operation. Desirably, the olefin stream contains not greater than about 10 wt % water, based on total weight of the olefin stream. Preferably, the olefin stream contains not greater than about 5 wt % water, and more preferably not greater than about 3 wt % water, based on total weight of the olefin stream.

In one embodiment of the invention, the olefin stream that is to be compressed and separated is relatively high in light olefins such as ethylene, propylene, and butylene. Preferably, the olefin stream has a substantial quantity of ethylene and propylene.

In one embodiment of the invention, the olefin stream that is to be compressed and separated comprises at least about 25 wt % ethylene, based on total weight of the olefin stream. Preferably, the olefin stream comprises from about 25 wt % ethylene to about 75 wt % ethylene, more preferably from about 30 wt % to about 60 wt % ethylene, and most preferably from about 35 wt % to about 50 wt % ethylene, based on total weight of the olefin stream.

In another embodiment, the olefin stream that is to be compressed and separated also comprises at least about 20 wt % propylene, based on total weight of the olefin stream. Preferably, the provided olefin stream comprises from about 20 wt % to about 70 wt % propylene, more preferably from about 25 wt % to about 50 wt % propylene, and most preferably from about 30 wt % to about 40 wt % propylene, based on total weight of the olefin stream.

It is desirable, but not required, that the provided olefin stream that is to be compressed and separated contain a relatively low concentration of ethane, preferably a lower concentration of ethane than propane, which can also be present. Preferably, the olefin stream comprises not greater than about 4 wt % ethane, more preferably not greater than about 3 wt % ethane, and most preferably not greater than about 2 wt % ethane, based on total weight of the olefin stream.

It is also desirable, but not required, that the provided olefin stream that is to be compressed and separated into olefin components contain a relatively low concentration of propane. Preferably, the olefin stream comprises not greater than about 5 wt % propane, more preferably not greater than about 4 wt % propane, and most preferably not greater than about 3 wt % propane, based on total weight of the olefin stream.

In another embodiment of the invention, the provided olefin stream that is to be compressed and separated into olefin components contains both ethylene and propylene. Desirably, the olefin stream contains at least about 50 wt % ethylene and propylene, based on total weight of the olefin stream. Preferably, the olefin stream contains from about 50 wt % to about 95 wt % ethylene and propylene, more preferably from about 55 wt % to about 90 wt % ethylene and propylene, and most preferably from about 60 wt % to about 85 wt % ethylene and propylene, based on total weight of the olefin stream.

III. Description of the Olefin Stream that is to be Compressed and Separated The olefin stream that is to be compressed and separated into olefin components can come from any source as long as the diene concentration is not too high. Such sources include cracking of hydrocarbons to form olefins, and catalytic conversion of oxygenates to olefins. Olefins obtained from the catalytic conversion of oxygenates to olefins are preferred as additional diene and other separation processes can be avoided. It is also acceptable to combine olefin streams from multiple sources as long as the diene concentration of the stream remains relatively low.

In one embodiment of the invention, the olefin stream that is to be separated into olefin components is obtained by contacting oxygenate with an olefin producing catalyst. Preferably, the olefin producing catalyst is a molecular sieve catalyst.

The oxygenate that is used in forming the olefin stream comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol includes an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; diisopropyl ether; formaldehyde; dimethyl carbonate; dimethyl ketone; acetic acid; and mixtures thereof. Preferred oxygenate compounds are methanol, dimethyl ether, or a mixture thereof.

Molecular sieves capable of converting an oxygenate to an olefin compound include zeolites as well as non-zeolites, and are of the large, medium or small pore type. Small pore molecular sieves are preferred in one embodiment of this invention, however. As defined herein, small pore molecular sieves have a pore size of less than about 5.0 angstroms. Generally, suitable catalysts have a pore size ranging from about 3.5 to about 5.0 angstroms, preferably from about 4.0 to about 5.0 angstroms, and most preferably from about 4.3 to about 5.0 angstroms.

Zeolite materials, both natural and synthetic, have been demonstrated to have catalytic properties for various types of hydrocarbon conversion processes. In addition, zeolite materials have been used as adsorbents, catalyst carriers for various types of hydrocarbon conversion processes, and other applications. Zeolites are complex crystalline aluminosilicates which form a network of $AlO_2$ and $SiO_2$ tetrahedra linked by shared oxygen atoms. The negativity of the tetrahedra is balanced by the inclusion of cations such as alkali or alkaline earth metal ions. In the manufacture of some zeolites, non-metallic cations, such as tetramethylammonium (TMA) or tetrapropylammonium (TPA), are present during synthesis. The interstitial spaces or channels formed by the crystalline network enable zeolites to be used as molecular sieves in separation processes, as catalyst for chemical reactions, and as catalyst carriers in a wide variety of hydrocarbon conversion processes.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof, but also materials which contain suitable replacement atoms for such silicon and aluminum atoms.

One type of olefin forming catalyst capable of producing large quantities of ethylene and propylene is a silicoaluminophosphate (SAPO) molecular sieve. Silicoaluminophosphate molecular sieves are generally classified as being microporous materials having 8, 10, or 12 membered ring structures. These ring structures can have an average pore size ranging from about 3.5 to about 15 angstroms. Preferred are the small pore SAPO molecular sieves having an average pore size of less than about 5 angstroms, preferably an average pore size ranging from about 3.5 to about 5 angstroms, more preferably from about 3.5 to about 4.2 angstroms. These pore sizes are typical of molecular sieves having 8 membered rings.

According to one embodiment, substituted SAPOs can also be used in oxygenate to olefin reaction processes. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an $AlPO_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aliminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of $MO_2$, $AlO_2$ and $PO_2$ tetrahedral units. These as manufactured structures (which contain template prior to calcination) can be represented by empirical chemical composition, on an anhydrous basis, as:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, MK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MIT, HEU, FER, AFO, AEL, TON, and substituted forms thereof. These small and medium pore molecular sieves are described in greater detail in the *Atlas of Zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition, according to an embodiment, preferably comprises from about 1% to about 99%, more preferably from about 5% to about 90%, and most preferably from about 10% to about 80%, by weight of molecular sieve. It is also preferred that the catalyst composition have a particle size of from about 20 angstroms to about 3,000 angstroms, more preferably from about 30 angstroms to about 200 angstroms, most preferably from about 50 angstroms to about 150 angstroms.

The catalyst can be subjected to a variety of treatments to achieve the desired physical and chemical characteristics. Such treatments include, but are not necessarily limited to, hydrothermal treatment, calcination, acid treatment, base treatment, milling, ball milling, grinding, spray drying, and combinations thereof.

A molecular sieve catalyst particularly useful in making ethylene and propylene is a catalyst which contains a combination of SAPO-34, and SAPO-18 or ALPO-18 molecular sieve. In a particular embodiment, the molecular sieve is a crystalline intergrowth of SAPO-34, and SAPO-18 or ALPO-18.

To convert oxygenate to olefin, conventional reactor systems can be used, including fixed bed, fluid bed or moving bed systems. Preferred reactors of one embodiment are co-current riser reactors and short contact time, countercurrent free-fall reactors. Desirably, the reactor is one in which an oxygenate feedstock can be contacted with a molecular sieve catalyst at a weight hourly space velocity (WHSV) of at least about 1 hr', preferably in the range of from about 1 hf$^{-1}$ to 1000 hr$^{-1}$, more preferably in the range of from about 20 hf$^{-1}$ to about 1000 hf$^{-1}$, and most preferably in the range of from about 50 hf$^{-1}$ to about 500 hr$^{-1}$. WHSV is defined herein as the weight of oxygenate, and reactive hydrocarbon which may optionally be in the feed, per hour per weight of the molecular sieve in the reactor. Because the catalyst or the feedstock may contain other materials which act as inerts or diluents, the WHSV is calculated on the weight basis of the oxygenate feed, and any reactive hydrocarbon which may be present with the oxygenate feed, and the molecular sieve contained in the reactor.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow with a relatively high content of oxygenated olefin by-products being found in the olefin product. However, the selectivity to ethylene and propylene at reduced temperatures may be increased. At the upper end of the temperature range, the process may not form an optimum amount of ethylene and propylene product, but the conversion of oxygenate feed will generally be high.

Operating pressure also may vary over a wide range, including autogenous pressures. Effective pressures include, but are not necessarily limited to, a total pressure of at least about 1 psia (7 kPa), preferably at least about 5 psia (34 kPa). The process is particularly effective at higher total pressures, including a total pressure of at least about 20 psia (138 kPa). Preferably, the total pressure is at least about 25 psia (172 kPa), more preferably at least about 30 psia (207 kPa). For practical design purposes it is desirable to use methanol as the primary oxygenate feed component, and operate the reactor at a pressure of not greater than about 500 psia (3445 kPa), preferably not greater than about 400 psia (2756 kPa), most preferably not greater than about 300 psia (2067 kPa).

Undesirable by-products can be avoided by operating at an appropriate gas superficial velocity. As the gas superficial velocity increases the conversion decreases avoiding undesirable by-products. As used herein, the term, "gas superficial velocity" is defined as the combined volumetric flow rate of vaporized feedstock, which includes diluent when present in the feedstock, as well as conversion products, divided by the cross-sectional area of the reaction zone. Because the oxygenate is converted to a product having significant quantities of ethylene and propylene while flowing through the reaction zone, the gas superficial velocity may vary at different locations within the reaction zone. The degree of variation depends on the total number of moles of gas present and the cross section of a particular location in the reaction zone, temperature, pressure and other relevant reaction parameters.

In one embodiment, the gas superficial velocity is maintained at a rate of greater than about 1 meter per second (m/s) at least one point in the reaction zone. In another embodiment, it is desirable that the gas superficial velocity is greater than about 2 m/s at least one point in the reaction zone. More desirably, the gas superficial velocity is greater than about 2.5 m/s at least one point in the reaction zone. Even more desirably, the gas superficial velocity is greater than about 4 m/s at least one point in the reaction zone. Most desirably, the gas superficial velocity is greater than about 8 m/s at least one point in the reaction zone.

According to yet another embodiment of the invention, the gas superficial velocity is maintained relatively constant in the reaction zone such that the gas superficial velocity is maintained at a rate greater than about 1 m/s at all points in the reaction zone. It is also desirable that the gas superficial velocity be greater than about 2 m/s at all points in the reaction zone. More desirably, the gas superficial velocity is greater than about 2.5 m/s at all points in the reaction zone. Even more desirably, the gas superficial velocity is greater than about 4 m/s at all points in the reaction zone. Most desirably, the gas superficial velocity is greater than about 8 m/s at all points in the reaction zone.

The amount of ethylene and propylene produced in the oxygenate to olefin process can be increased by reducing the conversion of the oxygenates in the oxygenate to olefins reaction. However, reducing the conversion of feed oxygenates in the oxygenate conversion reaction tends to increase the amount of oxygenated hydrocarbons, particularly including dimethyl ether, that are present in the olefin product. Thus, control of the conversion of feed to the oxygenate reaction process can be important.

According to one embodiment, the conversion of the primary oxygenate, e.g., methanol, is from about 90 wt % to about 98 wt %. According to another embodiment the conversion of methanol is from about 92 wt % to about 98 wt %, preferably from 94 wt % to 98 wt %.

According to another embodiment, the conversion of methanol is above about 98 wt % to less than about 100 wt %. According to another embodiment, the conversion of methanol is from about 98.1 wt % to less than about 100 wt %; preferably from about 98.2 wt % to about 99.8 wt %. According to another embodiment, the conversion of methanol is from about 98.2 wt % to less than about 99.5 wt %; preferably from about 98.2 wt % to about 99 wt %.

In this invention, weight percent conversion is calculated on a water free basis unless otherwise specified. Weight percent conversion on a water free basis is calculated as: 100× (weight oxygenate fed on a water free basis—weight oxygenated hydrocarbon in the product on a water free basis). The water free basis of oxygenate is calculated by subtracting out the water portion of the oxygenate in the feed and product, and excluding water formed in the product. For example, the weight flow rate of methanol on an oxygenate free basis is calculated by multiplying the weight flow rate of methanol by 14/32 to remove the water component of the methanol. As another example, the rate flow rate of dimethyl ether on an oxygenate free basis is calculated by multiplying the weight flow rate of diemethylether by 40/46 to remove the water component of the dimethyl ether. If there is a mixture of oxygenates in the feed or product, trace oxygenates are not included. When methanol and/or dimethyl ether is used as the feed, only methanol and dimethyl ether are used to calculate conversion on a water free basis.

In this invention, selectivity is also calculated on a water free basis unless otherwise specified. Selectivity is calculated as: 100× wt % component/(100-wt % water-wt % methanol-wt % dimethyl ether) when methanol and/or dimethyl ether is used as the feed.

The oxygenate to olefin process forms a substantial amount of water as a by-product. Much of this water by-product can be removed prior to distillation by cooling the stream to a temperature below the condensation temperature of the water vapor in the stream. Preferably, the temperature of the product stream is cooled to a temperature below the condensation temperature of the oxygenate feed. In certain embodiments it is desirable to cool the product stream below the condensation temperature of methanol.

It is desirable to cool the olefin stream from the oxygenate to olefin reaction process, then separate the cooled olefin stream into a condensed, water containing stream and an olefin vapor stream. The condensed, water containing stream comprises most of the water from the olefin stream, and a significant portion of the oxygenated hydrocarbons from the olefin stream. The olefin vapor stream comprises a majority of the olefins, e.g., ethylene and propylene. This olefin vapor stream will be in condition to send to the compressor system for compression and separation into olefin component streams. Such a stream will be have the acceptable diene content so that compressor fouling can be minimized.

A quench column is one type of equipment that is effective in cooling the olefin stream from the olefin to oxygenate reaction process. In a quench column, a quenching fluid is directly contacted with the olefin stream to cool the stream to the desired condensation temperature. Condensation produces the condensed water containing stream, which is also referred to as a heavy bottoms stream. The olefin portion of the olefin product stream remains a vapor, and exits the quench column as an overhead vapor stream. The overhead vapor stream is rich in olefin product, and can also contain some oxygenated hydrocarbon by-products as well as water.

In one embodiment, the quenching fluid is a recycle stream of the condensed water containing, heavy bottoms stream of the quench column. This water containing stream is desirably cooled, e.g., by a heat exchanger, and injected back into the quench column. It is preferred in this embodiment to not inject cooling medium from an outside source into the quench column, although it may be desirable to do so in other separation equipment down stream of the quench column.

IV. Compressing the Olefin Stream

In one embodiment of the invention, the olefin stream that is to be separated into at least two olefin streams is compressed in a compressor system having a first stage and a second stage. In the compression process, it is desirable that the compressed olefin stream exit the compressor system at both the first stage and the second stage at a temperature of not greater than about 260° F. (127° C.). Preferably, the compressed olefin stream exits the first stage and the second stage at a temperature of not greater than about 250° F. (121° C.). More preferably, the compressed olefin stream exits the first stage and the second stage of the compressor system at a temperature of from about 220° F. (104° C.) to about 260° F. (127° C.), more preferably at a temperature of from about 230° F. (110° C.) to about 250° F. (121° C.).

It is desirable in this invention that the olefin stream be compressed to a pressure which is effective for separating lighter olefins, particularly ethylene and propylene, from heavier olefins in a first stage separation vessel. In this regard, it is desirable that the compressed olefin stream exit the second stage of the compressor system at a pressure of at least about 175 psia (1,207 kPa). Preferably, the compressed olefin stream exits the second stage of the compressor system at a pressure of at least about 190 psia (1,310 kPa), more preferably at least about 200 psia (1,379 kPa). The second stage exit pressure is limited only by practical considerations, such as vessel thickness and expense of the compressor system. An upper pressure limit of about 500 psia (3,448 kPa) is a sufficient practical limit.

The pressure at which the olefin exits the first stage of the compressor system is only limited to the extent that the compressed olefin does not increase to an undesirably high temperature in the compression system, as high temperatures can degrade product quality and cause other system problems. However, it is desirable to balance the size of the two compressors used. In one embodiment, the olefin stream exits the first stage of the compressor system at a pressure of from about 75 psia (517 kPa) to about 150 psia (1,034 kPa); preferably a pressure of from about 80 psia (552 kPa) to about 140 psia (965 kPa); and most preferably a pressure of from about 90 psia (620 kPa) to about 130 psia (896 kPa).

V. Acid Gas Treating the Compressed Olefin Stream

In one embodiment of the invention, the olefin stream that exits the first stage of the compressor system is also treated to remove entrained acid gases such as $CO_2$ which may also be present in the olefin stream. Solid or liquid acid gas treatment systems can be used in this invention. In either system, the acid gas is removed from the compressed olefin stream by contacting the compressed olefin stream with an acid gas absorbent or adsorbent. Examples of such absorbents or adsorbents include amines, potassium carbonate, caustic, alumina, molecular sieves, and membranes, particularly membranes formed of polysulfone, polyimid, polyamide, glassy polymer and cellulose acetate. Solutions containing amines and caustic compounds are preferred, with caustic compounds being more preferred.

Aqueous amine solutions which are useful in this invention can contain any amine compound or compounds suitable for acid gas absorption. Examples include alkanolamines, such as triethanolamine (TEA); methyldiethanolamine (MDEA); diethanolamine (DEA); monoethanolamine (MEA); diisopropanolamine (DIPA); and hydroxyaminoethyl ether (DGA). Effective concentrations can range from about 0.5 to about 8 moles of amine per liter of aqueous solution.

Piperazine and/or monomethylethanolamine (MMEA) can be added to aqueous amine solutions to enhance their absorption capabilities. These additives can be included in the aqueous solution at a concentration of from about 0.04 to about 2 moles per liter of aqueous solution.

Caustic compounds which can be used in this invention are alkaline compounds which are effective in removing acid gas from an olefin stream. Examples of such alkaline compounds include sodium hydroxide and potassium hydroxide.

VI. Washing and Drying the Compressed Olefin Stream

Following acid gas treating, it is desirable to remove additionally entrained material in the treated compressed olefin steam using a water wash. Conventional equipment can be used.

This invention further includes an optional drying embodiment. In this embodiment, a solid or liquid drying system can be used to remove water and/or additional oxygenated hydrocarbon from the olefin stream that exits the second stage olefin compressor.

In the solid drying system, the compressed olefin stream is contacted with a solid adsorbent to further remove water and oxygenated hydrocarbon to very low levels. Typically, the adsorption process is carried out in one or more fixed beds containing a suitable solid adsorbent.

Adsorption is useful for removing water and oxygenated hydrocarbons to very low concentrations, and for removing oxygenated hydrocarbons that may not normally be removed by using other treatment systems. Preferably, an adsorbent system used as part of this invention has multiple adsorbent beds. Multiple beds allow for continuous separation without the need for shutting down the process to regenerate the solid adsorbent. For example, in a three bed system typically one bed is on-line, one bed is regenerated off-line, and a third bed is on stand-by.

The specific adsorbent solid or solids used in the adsorbent beds depends on the types of contaminants being removed. Examples of solid adsorbents for removing water and various polar organic compounds, such as oxygenated hydrocarbons and absorbent liquids, include aluminas, silica, 3 Å molecular sieves, 4 Å molecular sieves, and alumino-silicates. Beds containing mixtures of these sieves or multiple beds having different adsorbent solids can be used to remove water, as well as a variety of oxygenated hydrocarbons.

In this invention, one or more adsorption beds can be arranged in series or parallel. In one example of a series arrangement, a first bed is used to remove the smallest and most polar molecules which are the easiest to remove. Subsequent beds for removing larger less polar oxygenated species are next in series. As a specific example of one type of arrangement, water is first selectively removed using a 3 Å molecular sieve. This bed is then followed by one or more beds containing one or more less selective adsorbents such as a larger pore molecular sieve e.g. 13 X and/or a high surface area active alumina such as Selexorb CD (Alcoa tradename).

In another embodiment, the first bed is a 3.6 Å molecular sieve capable of selectively removing both water and methanol. This bed can then be followed by one or more 13 X or active alumina beds as described above.

The adsorbent beds can be operated at ambient temperature or at elevated temperature as required, and with either upward or downward flow. Regeneration of the adsorbent materials can be carried out by conventional processes including treatment with a stream of a dry inert gas such as nitrogen at elevated temperature.

In the liquid drying system, a water absorbent is used to remove water from the compressed olefin stream. The water absorbent can be any liquid effective in removing water from an olefin stream. Examples of water absorbents include alcohols, amines, amides, nitriles, heterocyclic nitrogen containing compounds, or a combination of any of the preceding. Either monohydric alcohols or polyhydric alcohols can be used as the alcohol absorbent. Specific examples of absorbents include methanol, ethanol, propanol, ethylene glycol, diethylene glycol, triethylene glycol, ethanolamine, diethanolamine, triethanolamine, hindered cyclic amines, acetonitrile, n-methylpyrrolidone, dimethyl formamide, and combinations thereof.

To obtain a substantial degree of effectiveness, the water absorbent should contain little non-water absorbing components. For example, the water absorbent should contain at least about 75 wt % water absorbing components. Desirably, the water absorbent contains at least about 90 wt %, preferably at least about 95 wt %, and most preferably at least about 98 wt % water absorbent.

Preferably the compressed olefin stream that is to be separated into olefin components is sufficiently dried before entering the separation vessel so that free water formation (i.e., formation of a separate water phase) or gas hydration does not significantly impede the separation process. Gas hydration results in the formation of clathrate compounds. Such compounds are solids, and these solids can cause significant operational problems in the separation process.

Water that is present in the compressed olefin stream that enters the separation vessel should be at a concentration sufficiently low such that a separate water phase is not formed during the separation process. This is particularly important when a distillation column having trays is used to separate the olefin components, since a separate water phase formed in the trays will impede mass transfer. Distillation columns having packing are preferred at higher concentrations of water, since such columns will not be prone to collect separate water phases.

It is desirable in this invention that the compressed olefin stream that is to be separated into olefin components contain not greater than about 10,000 wppm water, based on total weight of the olefin stream. Preferably the compressed olefin stream contains not greater than about 1,000 wppm water, more preferably not greater than 500 wppm water, and most preferably not greater than about 100 wppm water, based on total weight of the olefin stream.

It is not necessary in this invention that the compressed olefin stream be completely dry to separate into olefin components. That is, the compressed olefin stream can contain some water. The benefit of the olefin stream containing some amount of water is that additional and/or complex drying equipment will not be needed in order to separate the olefin stream into component products.

The compressed and optionally dried olefin stream is separated into olefin components using conventional separation equipment. For example, conventional distillation columns can be used.

VII. Ethylene, Propylene and Butylene Recovery and Derivative Processes

The olefin stream is desirably separated into olefin components so that high purity ethylene and propylene can be recovered. According to this invention, high purity is defined as at least about 95 wt %. Preferably, the ethylene and propylene streams comprise at least about 98 wt % ethylene or propylene, and most preferably at least about 99 wt % ethylene or propylene.

The ethylene and propylene streams separated according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these processes involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene and propylene, as well as $C_4^+$ olefins, particularly butylene, separated according to this invention. The olefins separated according to this invention can also be used in the manufacture of such compounds as aldehydes, acids such as $C_2$-$C_{13}$ mono carboxylic acids, alcohols such as $C_2$-$C_{12}$ mono alcohols, esters made from the $C_2$-$C_{12}$ mono carboxylic acids and the $C_2$-$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4^+$ olefins, butylene in particular, are particularly suited for the manufacture of aldehydes, acids, alcohols, esters made from $C_5$-$C_{13}$ mono carboxylic acids and $C_5$-$C_{13}$ mono alcohols and linear alpha olefins.

VIII. One Example of the Invention

One example of compressing an olefin stream is shown in the Figure. According to the Figure, an olefin stream is passed through a line 10 and sent to a first stage compressor 12. The olefin stream is compressed to a pressure of 105 psia (724 kPa), and the compressed olefin stream exits the compressor 12 through a line 14 at a temperature of 243° F. (117° C.).

The compressed olefin stream is sent through the line 14 to a caustic wash tower 16. A caustic solution is injected into the caustic wash tower 16 to contact the compressed olefin. The wash solution removes various non-olefin impurities such as $CO_2$ from the olefin stream, and the solution is removed from the caustic wash tower 16 through a line 20. Caustic washed olefin is removed from the caustic wash tower 16 through a line 22.

The caustic washed olefin is sent through the line 22 to a water wash tower 24. Water is injected into the water wash tower 24 to contact the olefin. The water removes additional non-olefin impurities as well as entrained caustic, and the water is removed from the water wash tower 24 through a line 28. Olefin is removed from the water wash tower 24 through a line 30.

The compressed olefin stream, having been caustic and water washed, is sent through the line 30 to a second stage compressor 32. The olefin stream is further compressed to a pressure of 315 psia (2,172 kPa). This further compressed stream exits the compressor 32 through a line 34 at a temperature of 248° F. (120° C.).

The compressed olefin in the line 34 is sent to a dryer bed 36, which contains a molecular sieve adsorbent for removing additional water and oxygenates from the compressed olefin stream. Following drying, the compressed olefin is sent through a line 38 to a separation system 40. Light olefin leaves the separation system 40 through a line 42, and heavy olefin leaves the separation system through a line 44.

Having now fully described this invention, it will be appreciated by those skilled in the art that the invention can be performed within a wide range of parameters within what is claimed, without departing from the spirit and scope of the invention.

The invention claimed is:

1. A process for making and separating an olefin stream comprising a mixture of olefins into at least two olefin streams, the process comprising the steps of:
    (a) providing an olefin stream to be separated comprising at least about 20 wt % of an olefin selected from the group consisting of ethylene, propylene and combinations thereof and not greater than about 3.0 wt % dienes based on the total weight of the olefin stream;
    (b) compressing the olefin stream in a compressor system having a first stage and a second stage to obtain a compressed olefin stream; and
    (c) separating the compressed olefin stream into at least two olefin streams,
    wherein the olefin stream being compressed in step b) is treated between the first stage and the second stage to remove acid gases prior to separating the compressed olefin stream into at least two olefin streams.

2. The process of claim 1, wherein the olefin stream to be separated comprises from at least about 50 wt % to about 90% ethylene and propylene based on the total weight of the olefin stream.

3. The process of claim 1, wherein the olefin stream exits the first stage of the compressor at a pressure of from about 75 psia (517 kPa) to about 150 psia (1,034 kPa), and exits the second stage of the compressor system at a pressure of at least about 175 psia (1,207 kPa), and the compressed olefin stream exits the compressor system at a temperature of from about 220° F. (104° C.) to no greater than about 260° F. (127° C.).

4. The process of claim 3, wherein the olefin stream to be separated is produced by the step of contacting an oxygenate with a molecular sieve catalyst comprising a silicoaluminophosphate or an aluminophosphate.

5. The process of claim 1, wherein the at least two olefin streams include (i) a light olefin stream comprising at least one olefin selected from the group consisting of ethylene, propylene and butylenes, and (ii) a heavy olefin stream comprising olefins that have boiling points that are, on average, higher than those in the light olefin stream.

6. A process for making and separating an olefin stream comprising a mixture of olefins into at least two olefin streams, the process comprising the steps of:
   a) providing an olefin stream to be separated comprising at least about 20 wt % of an olefin selected from the group consisting of ethylene, propylene and combinations thereof and not greater than about 3.0 wt % dienes based on the total weight of the olefin stream;
   b) compressing the olefin stream in a compressor system having a first stage and a second stage to obtain a compressed olefin stream, wherein the compressed olefin stream exits the first stage and the second stage a temperature of not greater than about 260° F. (127° C.) and exits the second stage a pressure of at least about 175 psia (1,207 kPa); and
   c) separating the compressed olefin stream into at least two olefin streams, wherein the olefin stream being compressed in step b) is treated between the first stage and the second stage to remove acid gases prior to separating the compressed olefin stream into at least two olefin streams.

7. The process of claim 1, wherein the treated olefin stream is further washed with water prior to separating into the at least two olefin streams.

8. The process of claim 6, wherein the process further comprises drying the compressed olefin stream formed in step b), prior to the separating in step c).

9. The process of claim 8, wherein the compressed olefin stream is contacted with an adsorbent to dry the compressed olefin stream.

10. The process of claim 6, wherein the at least two olefin streams include (i) a light olefin stream comprising at least one olefin selected from the group consisting of ethylene, propylene and butylenes, and (ii) a heavy olefin stream comprising olefins that have boiling points that are, on average, higher than those in the light olefin stream.

11. A process for making and separating an olefin stream comprising a mixture of olefins into at least two olefin streams, the process comprising the steps of:
   a) contacting an oxygenate with a molecular sieve catalyst to produce an olefin stream to be separated comprising at least about 20 wt % of an olefin selected from the group consisting of ethylene, propylene and combinations thereof and not greater than about 3.0 wt % diener based on the total weight of the olefin stream;
   b) compressing the olefin stream in a compressor system having a first stage and a second stage to obtain a compressed olefin stream, wherein the compressed olefin stream exits the compressor system at a temperature of not greater than about 260° F. (127° C.) and exits the second stage a pressure of at least about 175 psia (1,207 kPa); and
   c) separating the compressed olefin stream into at least two olefin streams,
   wherein the olefin stream being compressed in step b) is treated between the first stage and the second stage to remove acid gases prior to separating the compressed olefin stream into at least two olefin streams.

12. The process of claim 11, wherein the compressed olefin stream exits the first stage of the compressor at a pressure of from about 75 psia (517 kPa) to about 150 psia (1,034 kPa).

13. The process of claim 11, wherein the olefin stream to be separated comprises from at least about 50 wt % to about 90% ethylene and propylene based on the total weight of the olefin.

14. The process of claim 11, wherein the treated olefin stream is further washed with water prior to separating into the at least two olefin streams.

15. The process of claim 11, wherein the process further comprises drying the compressed olefin stream formed in step b), prior to the separating in step c).

16. The process of claim 11, wherein the at least two olefin streams include (i) a light olefin stream comprising at least one olefin selected from the group consisting of ethylene, propylene and butylenes, and (ii) a heavy olefin stream comprising olefins that have boiling points that are, on average, higher than those in the light olefin stream.

17. The process of claim 11, wherein the molecular sieve catalyst is a silicoaluminophosphate or an alum inophosphate.

18. A process for making and separating an olefin stream comprising a mixture of olefins into at least two olefin streams, the process comprising the steps of:
   a) providing an olefin stream to be separated comprising not greater than about 3.0 wt % dienes based on the total weight of the olefin stream;
   b) compressing the olefin stream in a compressor system having a first stage and a second stage to obtain a compressed olefin stream; and
   c) separating the compressed olefin stream into at least two olefin streams,
   wherein the olefin stream being compressed in step b) is treated between the first stage and the second stage to remove acid gases prior to separating the compressed olefin stream into at least two olefin streams.

19. The process of claim 18, wherein the olefin stream exits the first stage of the compressor at a pressure of from about 75 psia (517 kPa) to about 150 psia (1,034 kPa), and exits the second stage of the compressor system at a pressure of at least about 175 psia (1,207 kPa), and the compressed olefin stream exits the compressor system at a temperature of from about 220° F. (104° C.) to no greater than about 260° F. (127° C.).

20. The process of claim 18, wherein the treated olefin stream is further washed with water prior to separating into the at least two olefin streams.

21. The process of claim 18, wherein the process further comprises drying the compressed olefin stream formed in step b), prior to the separating in step c).

22. The process of claim 18, wherein the at least two olefin streams include (i) a light olefin stream comprising at least one olefin selected from the group consisting of ethylene, propylene and butylenes, and (ii) a heavy olefin stream comprising olefins that have boiling points that are, on average, higher than those in the light olefin stream.

* * * * *